United States Patent [19]
Matey et al.

[11] Patent Number: 5,649,021
[45] Date of Patent: Jul. 15, 1997

[54] METHOD AND SYSTEM FOR OBJECT DETECTION FOR INSTRUMENT CONTROL

[75] Inventors: James R. Matey, Mercerville; John G. Aceti, Cranbury; Timothy A. Pletcher, East Hampton, all of N.J.

[73] Assignee: David Sarnoff Research Center, Inc., Princeton, N.J.

[21] Appl. No.: 472,832

[22] Filed: Jun. 7, 1995

[51] Int. Cl.$^6$ .................................................. G06K 9/62
[52] U.S. Cl. ............................ 382/128; 382/165; 606/46; 348/65
[58] Field of Search ............................... 382/128, 164, 382/163, 165, 282, 291, 175, 317, 152, 100; 600/118, 134; 348/143, 156, 152, 65; 606/38, 39, 46

[56] References Cited

U.S. PATENT DOCUMENTS

| | | | |
|---|---|---|---|
| 3,683,923 | 8/1972 | Anderson | 128/303.14 |
| 3,897,787 | 8/1975 | Ikuno et al. | 128/303.14 |
| 4,094,320 | 6/1978 | Newton et al. | 128/303.14 |
| 4,184,492 | 1/1980 | Meinke et al. | 128/303.14 |
| 4,218,673 | 8/1980 | Yoshida | 340/146.3 MA |
| 4,303,073 | 12/1981 | Archibald | 128/303.13 |
| 4,422,457 | 12/1983 | Hattori | 606/39 |
| 4,539,585 | 9/1985 | Spackova et al. | 358/937 |
| 4,692,806 | 9/1987 | Anderson et al. | 358/209 |
| 4,742,815 | 5/1988 | Ninan | 128/4 |
| 4,793,345 | 12/1988 | Lehmer | 128/303.13 |
| 4,797,942 | 1/1989 | Burt | 382/41 |
| 5,063,603 | 11/1991 | Burt | 382/37 |
| 5,085,325 | 2/1992 | Jones et al. | 209/580 |
| 5,097,328 | 3/1992 | Boyette | 358/108 |
| 5,267,994 | 12/1993 | Gentelia | 606/15 |
| 5,312,401 | 5/1994 | Newton | 606/46 |
| 5,417,210 | 5/1995 | Funda et al. | 348/65 |
| 5,459,793 | 10/1995 | Naoi et al. | 382/165 |
| 5,534,917 | 7/1996 | MacDougall | 348/586 |
| 5,546,475 | 8/1996 | Bolle et al. | 382/164 |

OTHER PUBLICATIONS

"The Laplacian Pyramid As A Compact Image Code", Peter J. Burt et al., IEEE Transaction on Communications, vol. COM–31, No. 4, Apr., 1983.

"Object Tracking With A Moving Camera—An Application of Dnamic Motion Analysis", Proceeding of the Workshop on Visual Motion, Irvine CA, Mar. 20–22, 1989.

"Real Time Pyramid Transform Architecture", G. van der Wal et al., SPIE vol. 579 Intelligent Robots and Computer Vison (1985).

"Smart Sensing Within A Pyramid Vision Machine", Peter Burt, Proceedings of the IEE, vol. 76, No. 8, Aug. 1988.

*Primary Examiner*—Michael T. Razavi
*Assistant Examiner*—Jon Chang
*Attorney, Agent, or Firm*—William J. Burke

[57] ABSTRACT

An apparatus and method for controlling an instrument is provided. The device may be a cutting tool for use in surgery, or other type of device applied to transform a specific object located in a defined area. The apparatus comprises a marker having a predetermined color. The marker is applied to the specific device or tool to form a marked device. An imager generates video signals representing a color image of the defined area. A color detector processes the imager signals to detect a range of colors in the image represented by the imager signals. The range of colors includes the predetermined color. The color detector provides an output signal representing instances of signals in the detected color range. A detection mechanism processes the output signal of the color detector to provide an indication of whether the detected instances represented by the output signal conform to the marked device. A control mechanism disables the marked device if the detected instances do not conform to the marked device, in response to the indication provided by the detection mechanism.

17 Claims, 10 Drawing Sheets

METHOD AND SYSTEM FOR OBJECT DETECTION FOR INSTRUMENT CONTROL

The present invention relates generally to control apparatus and methods, and specifically to apparatus and methods for detecting an object within the field of view of an imager and controlling an instrument based on the signals generated by the imager.

BACKGROUND OF THE INVENTION

Imagers, such as a video cameras, are used extensively in control systems. The imager may provide a human operator with visual feedback for a remotely controlled procedure, or the imager may provide image input data that is processed by a pattern recognition facility to guide a completely automated process.

Video assisted techniques are used, for example, during surgery to minimize the size of the incision made in the patient's abdominal wall when examining the peritoneal cavity. These techniques include the use of laparoscopes and endoscopes (which may be, for example, arthroscopes). In conventional laparoscopy, a trocar sheath, for example, provides a conduit through the patient's skin into the peritoneal cavity. A tool, such as an electrosurgical tool is removably insertable through the trocar sheath. The tool includes an electrode having an active electrode probe at the distal end thereof. A variety of tip shapes have been used for the probe. The surgery is performed by operating the electrosurgical tool from the proximal end of the probe. Other surgical tools and energy sources (such as ultrasonic tools and argon assisted electrosurgical tools) may be used.

To guide the electrosurgical tool, the surgeon uses a laparoscope which employs a video camera to view the patient's tissue. Typically, the region of interest is illuminated and the color image is transmitted back to the video camera using optical systems inserted through one or more other trocar sheaths at other incisions in the patient's body. Thus, either the illumination source, or the viewing optical system may not always be directed to the same area as the electrosurgical tool during surgery.

During video assisted surgery, the surgeon may use the tool to cut, coagulate or blend tissue. These devices use very high voltages or intense light sources and may cause inadvertent burning. For an electrosurgical tool, burning may be caused by capacitive coupling insulation failure or direct contact between the tip of the tool and the patient's tissue. Direct contact occurs when the surgeon inadvertently or too quickly keys the instrument before having the tip in the correct location. The direct burn is the most severe burn of the three types because it directs a full dose of power to the closest tissue.

The surgeon only sees what is in the field of view of the viewing instrument. However, tools are often out of the field of view, especially when the viewing instrument is brought into a close view of the area of interest. The likelihood of accidentally burning the patient is greater when the electrosurgical tool tip is outside of the field of view of the viewing instrument.

Although the description presented above is in the context of video assisted surgical procedures, the same type of problems may occur in other video assisted operations, for example, operations in which robotic devices must perform tasks because the environment is inhospitable to humans.

SUMMARY OF THE INVENTION

The present invention is an apparatus and method for controlling an instrument. The device is applied to transform a specific object located in a defined area.

The apparatus comprises a marker having a predetermined color. The marker is applied to the specific device to form a marked device. An imager, such as a video camera, generates imager signals representing a color image of the defined area. A color detector processes the video signals to detect a range of colors in the image represented by the video signals. The color detector provides an output signal representing instances of signals in the detected color range. A detection mechanism processes the output signal of the color detector to provide an indication of whether the detected instances represented by the output signal conform to the marked device. A control mechanism disables the marked device if the detected instances do not conform to the marked device, in response to the indication provided by the detection mechanism.

Another aspect of the invention is a method for controlling an instrument that is applied to transform a specific object located in a defined area. A marker having a predetermined color is applied to the specific device to form a marked device. Imager signals which represent a color image of the defined area are generated. A range of colors are detected in the image represented by the imager signals. The range of colors includes the predetermined color. An output signal representing instances of signals in the detected color range is formed. The output signal is processed to provide an indication of whether the output signal of the color detector conforms to the marked device. The marked device is disabled if the indication identifies the marked device as being outside the defined area.

DETAILED DESCRIPTION

Figure 1:
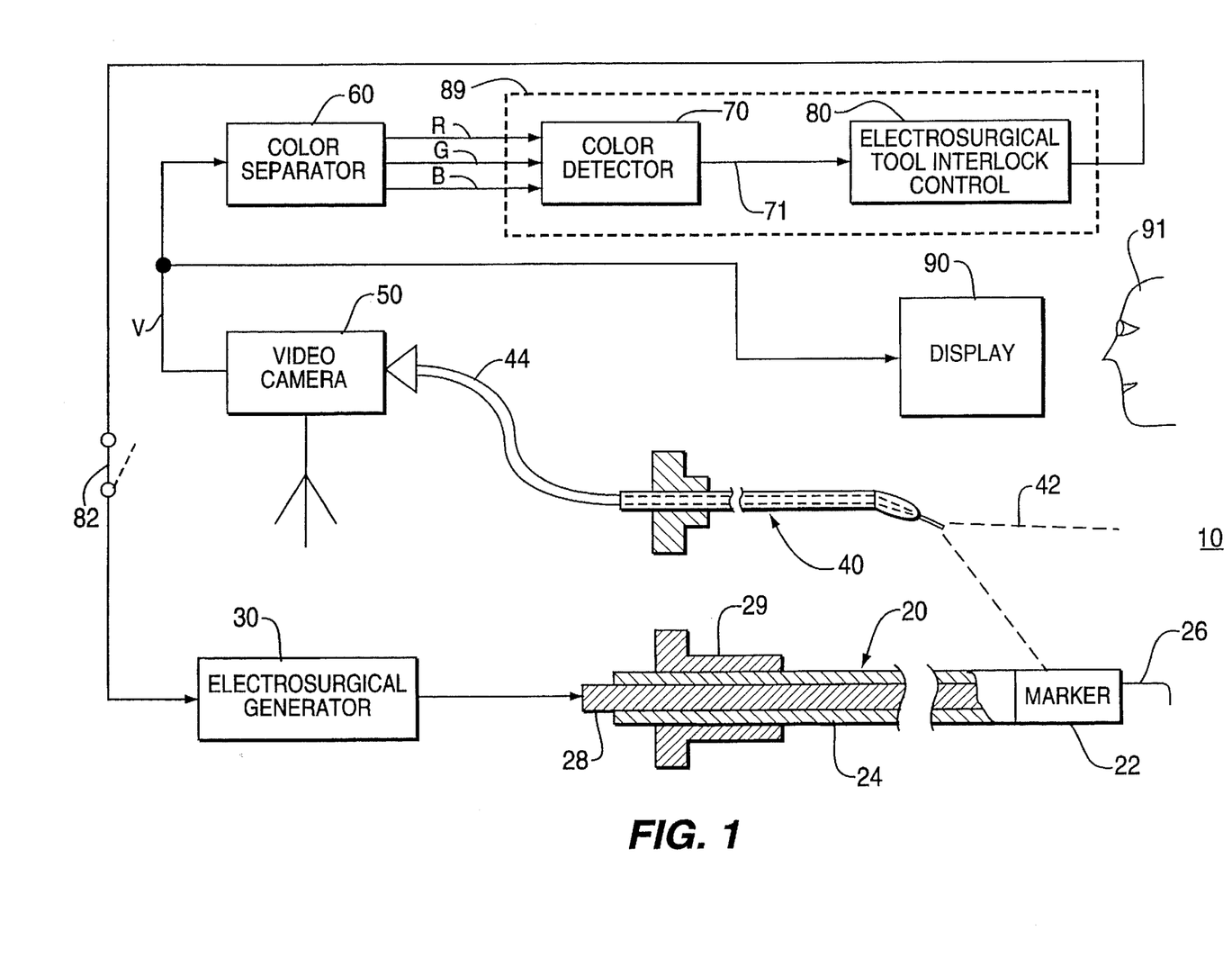
FIG. 1 is a schematic diagram of an apparatus of the invention.

FIG. 1 is a schematic view of an imager assisted procedure apparatus, commonly known as a video assisted procedure (VAP) apparatus, according to the invention. The VAP apparatus may use, for example, a viewing instrument such as an endoscope, arthroscope or laparoscope but other scopes may equally well be used. It may also be an instrument which is used to perform operations using robotic manipulations. In FIG. 1, an interlock system 10 designed for a surgical cutting tool 20 uses color to detect the presence of the tool 20 during a laparoscopy procedure. The apparatus 10 prevents a surgeon using the tool 20 from activating the generator 30 supplying power to the tool 20 unless the tool 20 (as described in the next paragraph) is in the field of view 42 of the laparoscope 40 used to view the procedure, as monitored by an imager 50, such as a color TV camera, coupled to the laparoscope 40.

A marker 22 having a predetermined color is applied to a specific device (which in this case is an electrosurgical tool 20), to form a marked device. The imager 50 generates video signals V representing a color image of a defined area within the field of view 42 of laparoscope 40.

Preferably, the color of marker 22 is substantially different from the background of the scene. The system is trained by determining colors normally found in the scene. A color not normally found in the scene is then selected. Preferably, the marker color used for video assisted surgical procedures is in a range of colors (wavelengths) outside the color space found in the body.

A color separator 60 processes the video signals V to detect the colors in the image represented by the video signals. A range of colors which includes the predetermined color is detected. The color separator provides output signals R, G and B representing red, green and blue component colors signals in the image.

Alternatively, another color separation scheme such as Hue-Saturation-Luminance (HSL) or other technique well known to those of ordinary skill in the art may also be used. Furthermore, instead of separating the light into R, G and B components, the light may be separated into cyan, magenta and yellow components, or other components which span the color space.

A detection mechanism 70 processes the output signals R, G and B of the color separator 60 to provide an indication 71 of whether the detected instances represented by the output signals R, G and B correspond to the predetermined color.

In response to the indication 71 provided by the detection mechanism 70, a control mechanism 80 disables the tool 20 if the detected instances do not conform to the tool 20.

As shown in FIG. 1, the surgeon 91 views the operation on a monitor display 90 coupled to the imager 50. The imager 50 is coupled to the proximal end of the laparoscope 40 by an optical system 44. The imager 50 transmits the composite video electronic signal V which drives the display 90. This signal V may conform to an industry wide standard such as CCIR (European standard) or NTSC (U.S. standard), but other standards such as S-Video may also be used. The signal V includes both luminance and chrominance data for each pixel in the array. As shown in FIG. 1, the composite video signal V supplied from imager 50 is also input to the interlock detection system 10. If the tool 20 has a unique color marker thereon—one not found in the interior of the abdomen such as pure blue or pure green—then the presence of the tool 20 may be readily detected. The inventors have determined that blue is a preferred color.

The composite video signal V is first passed through color separator 60. The color separator 60 may be a commercially available integrated circuit (For example, the TDA3556 manufactured by the Phillips Corporation, or the TDA3330 manufactured by Motorola Corp. Inc.) which separates the composite video information into its three primary color components (i.e. Red, Green, and Blue). The color separated video signals R, G and B are then passed through the color detector circuit 70. Color detector 70 measures the ratio of the three primary colors with respect to one another. If there is a match between this ratio for the color viewed by the camera and the corresponding ratio for the color for which the control system 89 is searching, this event is recorded. The recorded instances of detection of the predetermined color are subsequently used to determine whether the marked cutting tool 20 is within the field of view 42 of the laparoscope 40. This process is repeated sixty times per second for conventional NTSC video signals (the rate at which the camera updates a field of imagery). A variety of detection algorithms may be used to detect the tool and are described in detail below.

The electrosurgical tool 20 for laparoscopic surgery, is a simple device. Any conventional electrosurgical tool configuration may be used, so long as the predetermined unique color is applied to mark the tool 20. The tool 20 has a long tubular sheath 24 and may include one of a variety of end effectors 26. The end effectors may be of conventional shapes, such as, for example, forceps, knife or hook like (not shown). In almost all cases the effectors 26 are made from metal, typically stainless steel. The tubular sheath 24 is an insulating material, typically plastic, which protects the internal wires 28, if present, prevents electrical arcing and provides a smooth surface for sealing in the trocar 29. The tubular sheath 24 extends to the active tip 26. The tubular sheath may be painted or dyed, or a tape may be applied to give it the unique color. Either the entire sheath or a fraction of the distal end (as shown in FIG. 1) may be colored. It is desirable that, at least the portion of the sheath containing the marker color be hydrophobic to prevent shading or hue shifting of the marker color from bodily fluids. The marker 22 may be applied to the tool 20 inexpensively by virtually any instrument manufacturer.

The control system 89 comprises a color marker detection mechanism 70 (hereafter detection mechanism 70) and an electrosurgical tool interlock control mechanism 80 (hereafter, control mechanism 80). The detection mechanism 70 scans the chroma portion (R, G and B) of the camera signal for the unique color at television frequencies (30 times per second). If the unique color is detected, then a positive signal 71 is transmitted from detection mechanism 70 to the control mechanism 80.

The detection mechanism 70 also includes means for verifying that more than a single pixel has the unique color, to prevent actuation of the tool 20 while the tool 20 is out of the field of view 42 (which could otherwise occur in the presence of electronic noise).

The inventors have determined that if either a blue or green marker 22 occupies at least 1.5% of the field of view of the camera, the signal to noise ratio is sufficient so that the probability of detection for blue and green markers is greater than 99%.

The control mechanism 80 either prevents or permits power to flow from the electrosurgical generator 30 to the tool 20. The control mechanism circuitry 80 may be integrated into the electronic circuitry of generator 30. A manual override mechanism 82 may be provided to allow the tool 20 to be operated regardless of whether the tool 20 is within the field of view 42 of the laparoscope. Thus, if the detection mechanism 70 fails for any reason, the tool 20 may be maintained operable by actuating the manual override switch 82.

The color of an object is determined by a number of physical parameters. First, because the frequency range of interest is typically in the visible spectrum, the tool's reflectances in each of the primary color bands are the primary contributors to the color of the tool 20. That is, the perceived color is directly proportional to the reflectance of tool 20 in each of the primary color bands. (Alternatively, the marker 22 may be a light emitting material).

Equally important is the color of the light that is used to illuminate the object. The perceived color of an object is directly proportional to the relative intensity of each of the primary colors irradiated onto the object in the scene and is, in fact, equal to the product of the object reflectance and irradiance. The relative illumination intensities (i.e., with respect to the primary color bands) vary from light source to light source. An inventory of the available illumination systems is performed and the color temperature or output spectrum from each is collected. From these data, an analysis may be performed to determine the effect on the variance of the perceived object colors due to lighting conditions. For example, an analysis as described in this paragraph was performed for the expected color space in video assisted procedures. This analysis is described below with reference to FIGS. 7–11.

The marker 22 must be large enough to be detected, but not so large as to fill the entire field of view of the camera system 50. A marker 22 that fills 1.5% of the total field of view can provide a 2:1 signal to noise ratio sufficient for detection.

The last parameter of significance with respect to object color representation is the sensitivity of camera system 50 to each of the primary color bands. It is assumed that the camera system 50 used to practice the invention preferably closely reproduces the spectrum as defined by the television standards.

The detection algorithm used for this implementation must be highly reliable from two different perspectives. First, to be an effective interlock system 10, the algorithm must minimize the probability of a false alarm when the tool 20 is not in the field of view of the imager 50. That is, system 10 should not indicate that tool 20 is present if the tool is, in fact, obscured or removed from the field of view 42 of laparoscope 40. Second, when the tool 20 is present in the field of view 42, system 10 must minimize the probability that the tool is not detected. Otherwise, the surgeon 91 is likely to override the interlock system 10.

Ideally, the marker 22 is formed of a material having a color signature, such that under "typical" illumination conditions, there is zero probability of identifying the marker 22 as being detected unless the chosen material is present. This would permit the simplest of detection circuits. A single instance of detecting such a color would indicate that the tool is present and could subsequently be used to alert the control mechanism 80 to this condition.

However, due to the expected variances in the illumination sources and detector sensitivities, it is not likely that such a combination of color and lighting conditions may be practically achieved. Therefore, it is practical to use a range of colors (light wavelengths) for the marker color. It is assumed that some portion of the color space of video assisted procedures has a relatively low, but finite probability of occurrence. Then, an alternative to the single instance detection method described above is one designed around the following criteria:

First, the color detector searches and finds a small, yet well defined, range of colors which have been determined to have the following features:

1) a low probability of occurrence during "typical" video assisted procedures, and 2) the same color space assigned to the cutting tool 20.

The control mechanism 89, having found picture elements of the appropriate color, then use additional information such as total energy content of the detected color (i.e., pixel counting) or a more complex method (such as, for example, spatial feature extraction) to determine with a high degree of confidence the presence of the cutting tool 20.

Additionally, the system 10 may be operated in an electrically hostile environment where interference (EMI and RFI) is likely to be high. The circuits used for detection mechanism 70 and control mechanism 80 should be designed to reject most of this noise, using techniques that are well known to one of ordinary skill in the art.

Figure 2:
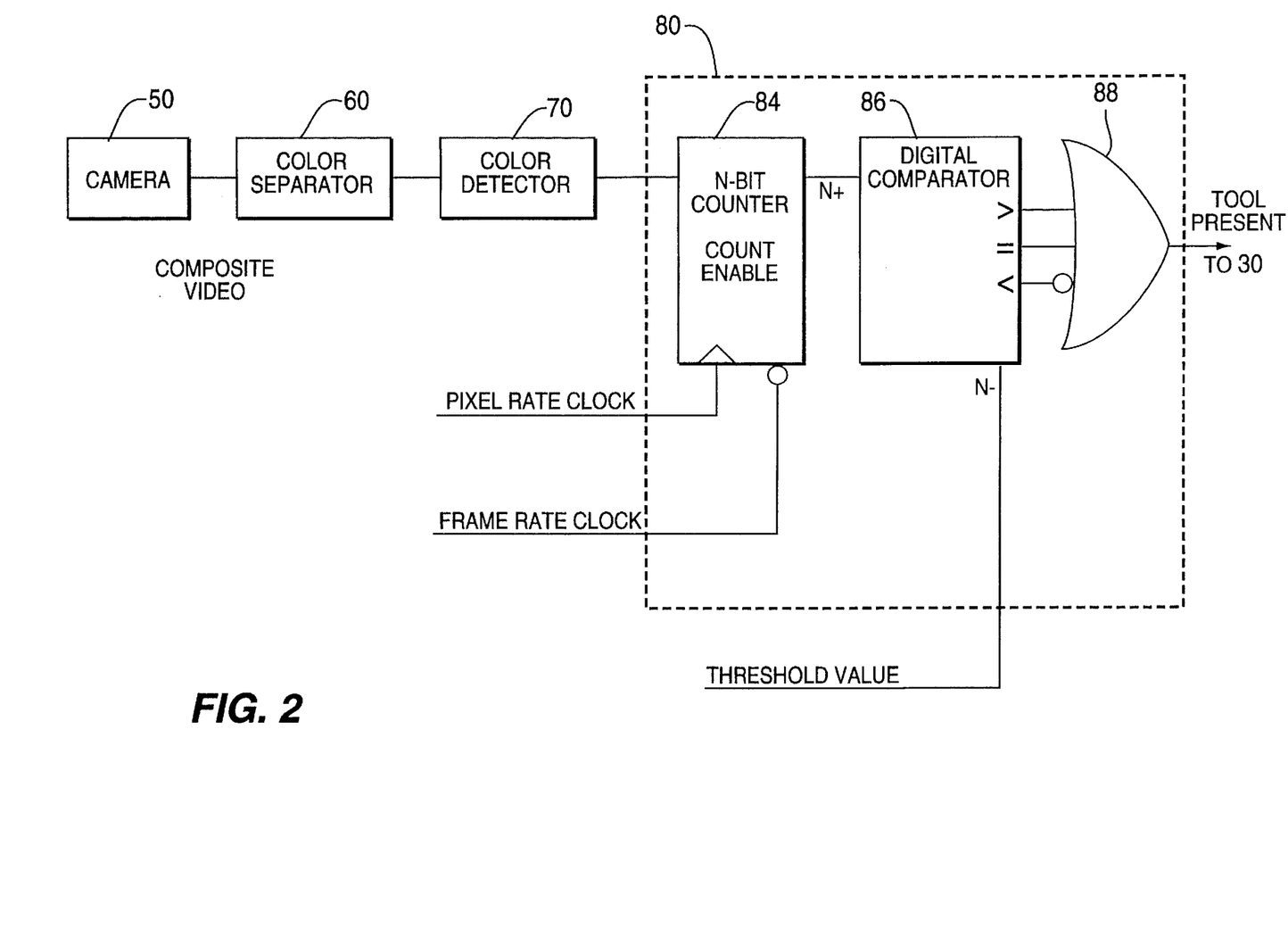
FIGS. 2–4 are a block diagrams of different embodiments of the control mechanism shown in FIG. 1.

FIG. 2 is a block diagram of a first embodiment of the control system 89. In FIG. 2, control mechanism 80 includes: means 84 for counting a number of pixels in the predetermined color range within a single frame of the video signals, based on the output signal of color detector 70; and means 86 and 88 for indicating that the detected instances conform to the marked device 20 if the number of pixels exceeds a predetermined threshold value. The indicating means includes a digital comparator 86 that compares the number of pixels to the predetermined value and to a logic-low state otherwise. An OR gate 88 is set to the logic high state if the number of pixels is greater than or equal to the predetermined value. The logic high state indicates that the marked device 20 has been detected. It has also been determined by the inventors that probability of detection is enhanced if the total luminance (i.e. R+G+B) is computed and compared against a minimum threshold.

The color selected for the cutting tool 20 is assumed to have a low probability of natural occurrence within the field of view of the imaging system. For video assisted surgical techniques, the preferred color is pure blue. Due to system noise, each picture element (pixel) has some finite probability of indicating the tool 20 is present. Over the course of a full frame, the number of pixels falsely indicating marked tool presence may be estimated by multiplying the total number of pixels in a frame by the probability of a positive indication arising from system noise. The sum of these products divided by the total number of picture elements represents the average number of noise pixels during the course of a "typical" frame, while the tool 20 is not present. This value is then used to calculate the detection threshold for tool 20. A practical threshold value (signal to noise ratio greater than 2:1) is set as a function of the noise variance and is selected to minimize the probability of false alarms.

In FIG. 2, when the tool 20 is within the field of view 42, the probability of the marked cutting tool color being found in that frame increases dramatically. The actual number of pixels detected varies as the fraction of the field of view of the viewing system subtended by the marked tool varies, for example because of the magnification or obscuration of tool 20.

As used herein, the term "sampling rate" is defined as either:

CCD rate=(No. of pixels/line)(No. of lines)(No. frames/sec.) for sampling a video signal comprising pixels; or Analog signal rate=(No. samples/line)(No. lines)(No. frames/sec.) for sampling an analog video signal.

The N-bit counter 84 is reset at the beginning of each frame. The counter 84 is incremented with each positive output of the detector 70. A digital comparator 86 compares the pixel count to the threshold value (set to a signal to noise ratio of 2:1). and provides an output signal to an OR gate 88. If the count is greater than or equal to the threshold, then OR gate 88 produces a logic high state, indicating that the tool 20 is present.

Figure 6:
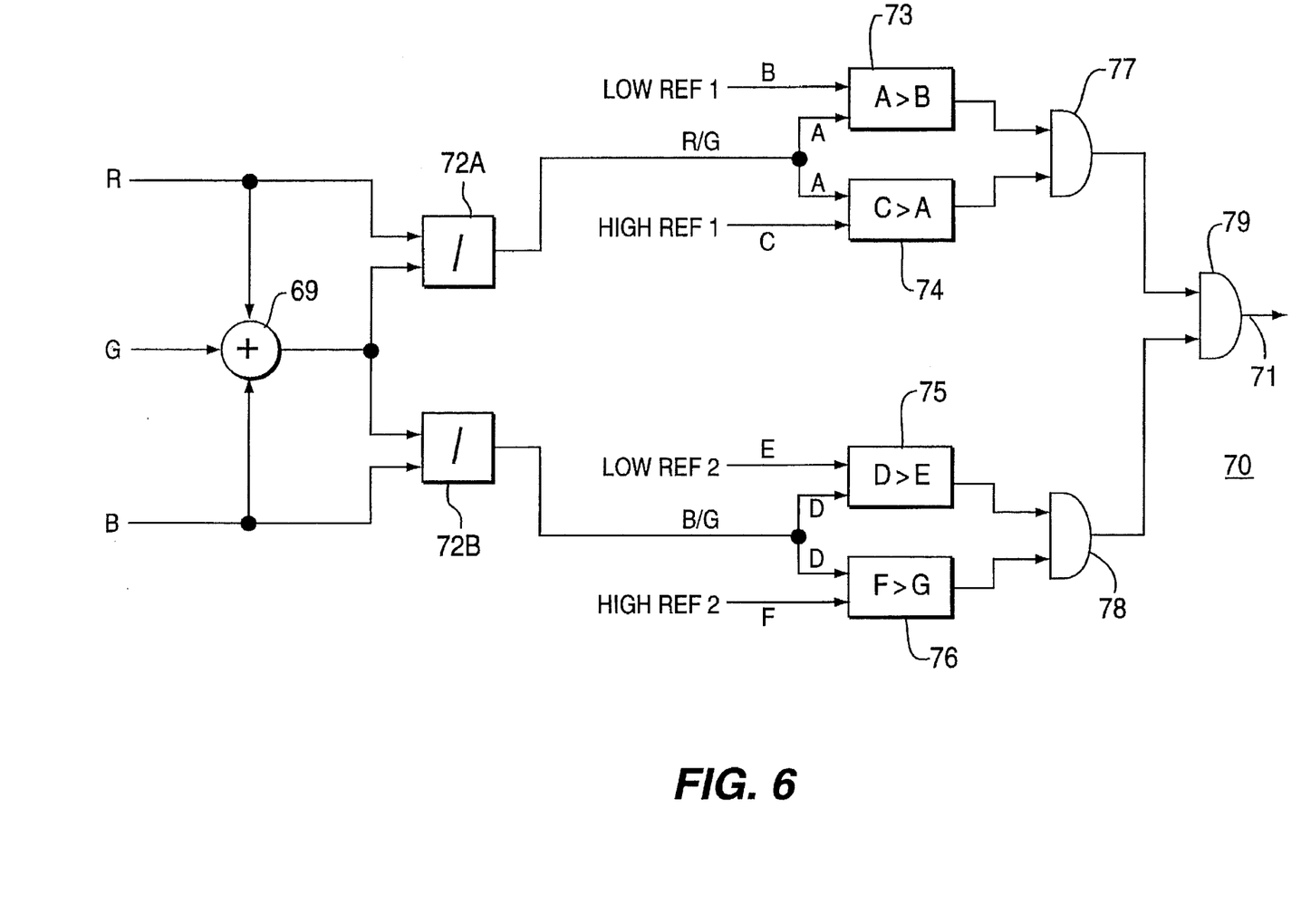
FIG. 6 is a block diagram of the color detector shown in FIG. 2.

FIG. 6 is a block diagram of a color detector circuit 70. Circuit 70 receives the R, G and B signals from color separator 60. The components R, G and B are added in adder 69, and the relative intensity of each component is determined in dividers 72A and 72B. For example, dividers 72A and 72B form respective ratios r=R/(R+B+G) and b=B/(R+B+G). R/(R+B+G) is then transmitted to comparators 73 and 74, and B/(R+B+G) is transmitted to comparators 75 and 76. Comparators 73 and 74 determine whether R/(R+B+G) is greater than a first minimum value LOWREF1 and less than a first maximum value HIGHREF1. The output signals from comparators 73 and 74 are provided to AND gate 77. If both comparator output signals are TRUE, then AND gate 77 transmits a logic high signal to AND gate 79. Similarly, Comparators 75 and 76 determine whether B/(R+B+G) is greater than a second minimum value LOWREF2 and less than a second maximum value HIGHREF2. The output signals from comparators 75 and 76 are provided to AND gate 78. If both comparator output signals are TRUE, then AND gate 78 transmits a logic high signal to AND gate 79. Thus if both R/(R+B+G) and B/(R+B+G) are within their respective ranges, both input signals to AND gate 79 are in the logic high state, and the output signal of AND gate 79 is in the logic high state to indicate that the predetermined color has been detected.

Figure 3:
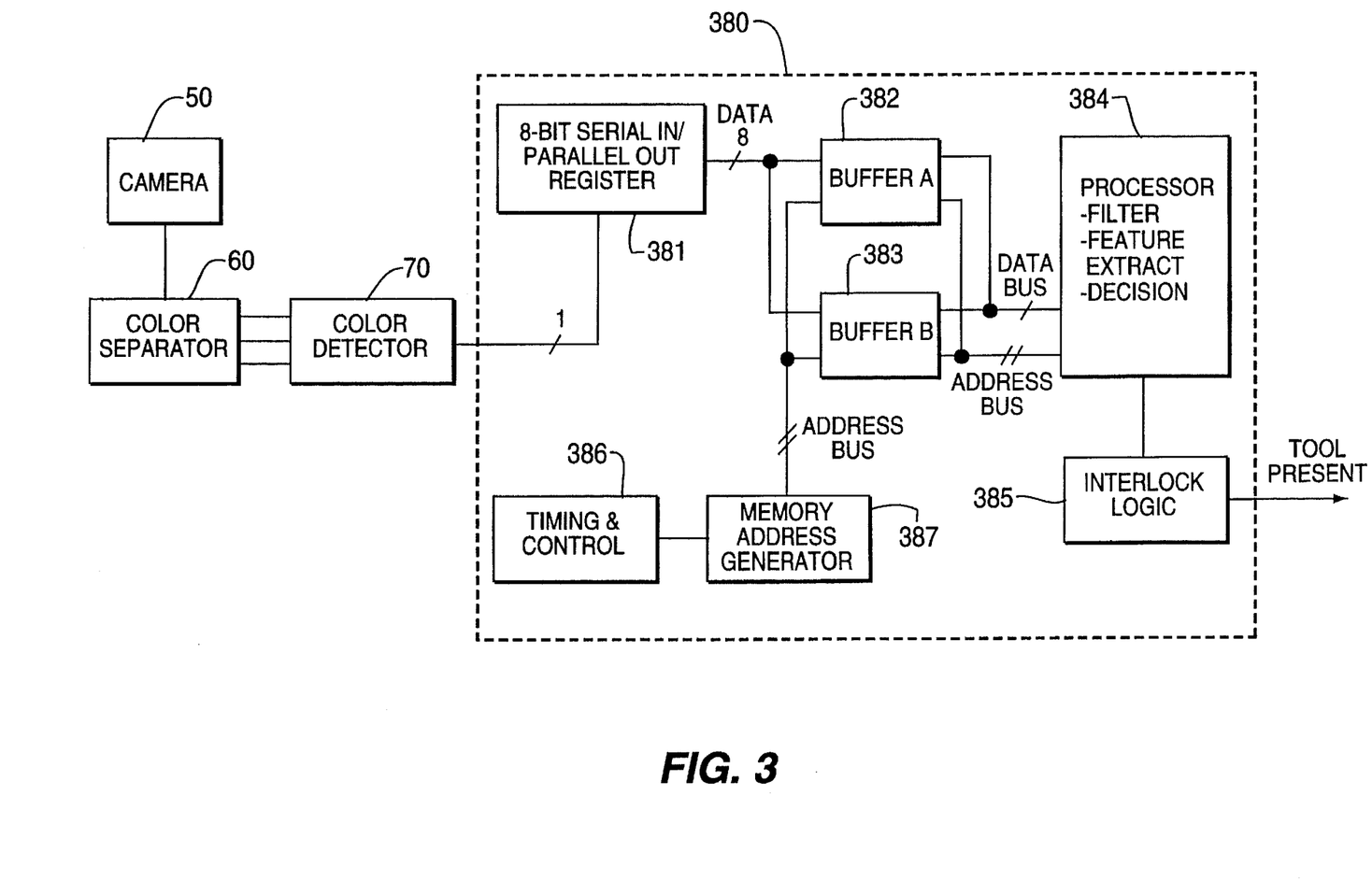

FIG. 3 is a block diagram showing a control mechanism 380 which is a more sophisticated variant of the pixel counting approach of FIG. 2, and is augmented by the use of spatial feature extraction. Rather than simply counting the number of detected pixels in a frame, only those pixels determined to be located within the estimated contour of the tool 20 are counted for the purposes of detecting the tool 20. The probability of detecting pixels possessing both the color and the estimated contour of the tool 20 while the tool 20 is not present is much lower than the probability of detecting a pixel having only the color of the tool 20 while the tool is not present. This effect decreases the probability of a false alarm. Although the embodiment of FIG. 3 provides a more reliable detection apparatus and method, this approach adds complexity to the system.

In FIG. 3, processor 384 (which may be a microprocessor or digital signal processor) is used for the decision making capabilities needed for spatial feature extraction. The output signal of the detector 70 is a binary image indicating by pixel whether the predetermined color is present or not. The general approach for extracting spatial information from a binary image is to copy the image into a computer memory, such as frame store or RAM, of sufficient size to store addresses of each pixel having the predetermined color. The memory may be accessed by both the processor 384 and the detector 70 to write to memory.

The output signal of detector 70 is transmitted to a register 381 as a one bit wide serial data stream. Register 381 receives the one bit stream, and provides an eight bit wide output terminal, from which the data are transmitted to the memory.

The memory may be arranged as shown in FIG. 3, wherein the memory comprises a circular buffer having two parts 382 and 383. The two parts of the memory space (buffer A 382 and buffer B 383) may be simultaneously written to by the detector 70 and accessed by the processor 384. Thus, detection circuit 70 can write to one of the buffers 382, 383 while processor 384 reads from the other buffer. A timer 386 and memory address generator 387 are provided to synchronize the memory accesses.

In processor 384 the color detected image is passed through a series of spatial filters to increase the signal to noise ratio for the tool specific spatial contour. Filtering of this type usually takes the form of a bandpass characteristic designed from a priori knowledge of the size of tool 20 and the expected range of magnification of the tool 20 during the course of a video assisted procedure. The image resulting from the filtering operations may then be analyzed using any of a variety of conventional filtering techniques which are well known in the art, such as (but not limited to) a clustering procedure in conjunction with one or more spatial features extracted from the image (e.g., cluster area, first and second order moments, Fourier descriptors, etc.).

In a method using Fourier descriptors, the edges of the marker 22 are determined by sampling. The X and Y coordinates of each pixel on the edge of the marker 22 are automatically determined in situ. A fast Fourier transform operation is then performed on the X-Y coordinate data with the X axis coordinate corresponding to the real component of the value and the Y axis coordinate corresponding to the imaginary component of the value. The result of the transform includes a plurality of coefficients; the first coefficient (the DC component) represents the center of gravity of the object. The remaining coefficients correspond to higher spatial frequencies. These components may then be correlated with the image data viewed during an actual video assisted procedure. If the correlation is sufficiently high, the object viewed is identified as the marker 22.

Another method for identifying the marker 22 is to compute first and second order area moments of the portion of the image comprising the marker 22. The first order moment defines the area and centroid of the marker 22. The second order moment (the area moment of inertia) defines the variance of the contour of marker 22 with respect to each axis. When an object is viewed during the video assisted procedure, the first and second moments of the object may be computed and compared to the known first and second order moments for the marker. One of ordinary skill will recognize that area moment of inertia is represented by a tensor quantity, and varies with the choice of axes (or orientation of the tool or object). Determination of the principle axes and the corresponding moments of inertia is a well known characteristic value (Eigenvalue) problem. Thus the moments about the principle axes may be determined, both for the marker 22, and for the object in the field of view 42 of laparoscope 40. This method may be computationally simpler than the Fourier descriptor technique.

An alternative method involves the use of Hough transforms, which may readily be performed by one of ordinary skill in the art.

An alternative method is defined in U.S. Pat. No. 5,063,603 to Burr, which is expressly incorporated herein by reference for its teachings on techniques for recognition of objects of a specific class within a frame of video information. Using the method of U.S. Pat. No. 5,063,603, distinguishing features of the marker 22 are stored in a template. For example, the target image may be subjected to a pyramid processing technique, and the laplacian images for each sub-band of frequencies may be stored in the template.

During recognition, a multi-resolution processor generates a plurality of images from the original image. At each level of the pyramid a Laplacian image, based on the image at the previous level of the pyramid is obtained. Each of these images has a lower resolution and sample density than the image at the previous level. As part of the correlation function, the data in the field of view 42 are compared to the images in the template. Beginning at the lowest resolution image in the pyramid, processor 384 computes the match between the image and the template. The orientation of the image may be rotated iteratively, until an orientation that produces the best match is found. If the determined match is sufficiently close to continue, but not close enough to positively identify the tool 20, then the next higher resolution image in the pyramid is compared to the template. Successively higher resolution images are compared with the template, until the calculated match is close enough to positively identify the tool 20. Once the tool is positively identified, logic 385 enables the electrosurgical generator 30 (shown in FIG. 1).

The operation of the spatial feature extraction recognition procedures may be enhanced if the probe tip is marked with a predetermined distinctive shape that has the selected color. One such shape may be a bulls eye design which is advantageous because it has similar spatial frequency spectra at different sizes and does not need to be rotated to be detected. To ensure that the tool can be identified, it may be desirable to mark the tool at several points about its circumference with the distinctive shape.

Figure 4:
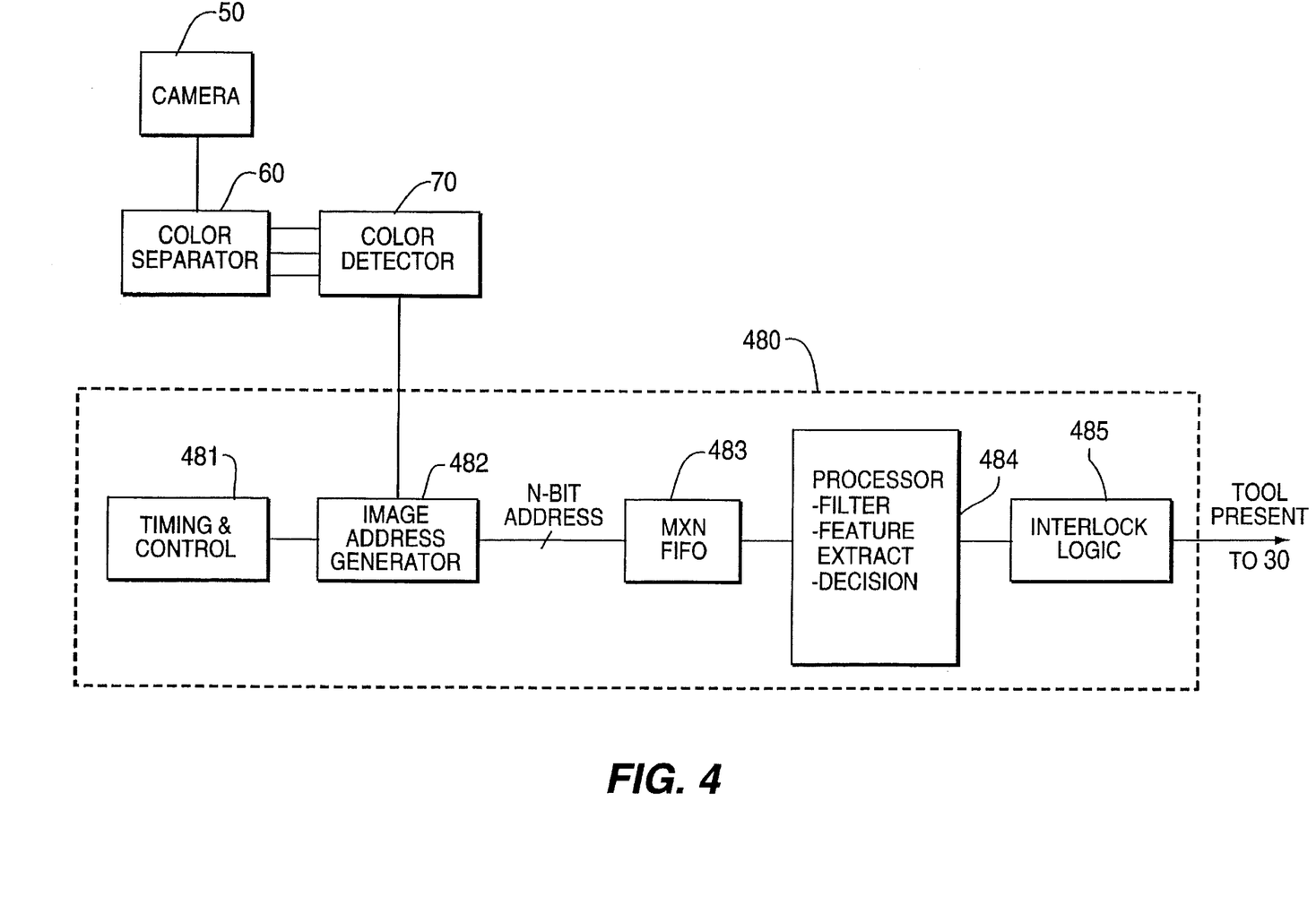

FIG. 4 shows another embodiment of the invention, employing an alternative architecture. In the system of FIG. 4, the control mechanism 480 passes a reconstructed pixel address to the processing unit 484. Instead of processing the entire image to search for the tool 20, an M pixel by N pixel region is selected, and the addresses of the detected pixels within the M×N region are stored in an M×N FIFO queue 483. The portion of the image defined by the addresses in queue 483 may be searched by any of the above techniques.

The method of FIG. 4 works in the same way as the method of FIG. 3, but decreases the storage requirement and the analysis times from that of the full image to that of several pixels. The embodiment of FIG. 4 also increases the fraction of processor time dedicated to processing the image, because the processor spends a smaller fraction of the time retrieving the image data. The subsequent processing of the image data closely follows that described in the embodiment of FIG. 3.

Figure 5:
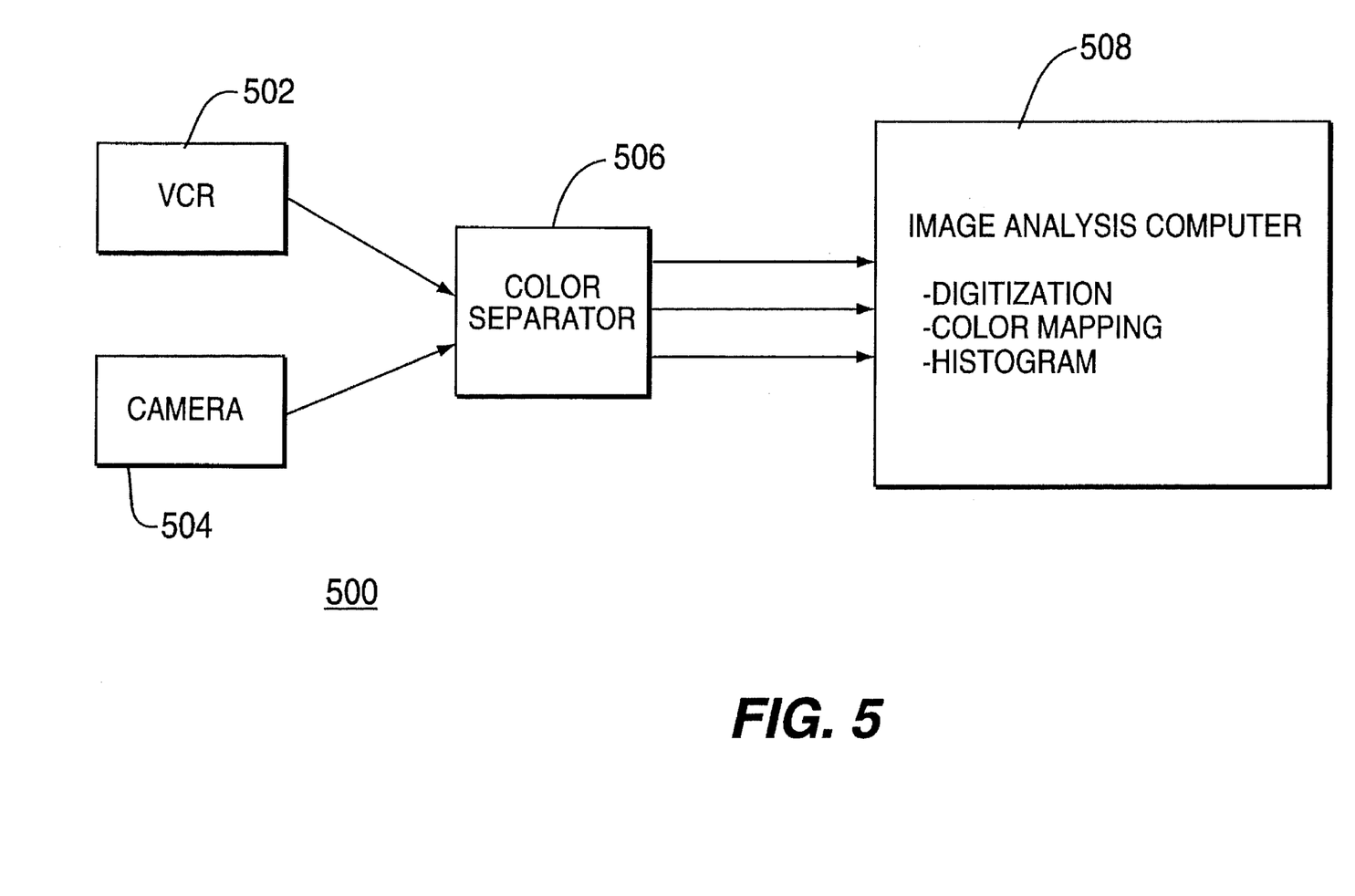
FIG. 5 is a block diagram of apparatus for collecting training data used by the apparatus of FIG. 1.

In FIG. 5, apparatus 500 for collecting training data used by the apparatus 10 of FIG. 1 is shown. To obtain the appropriate information needed to develop the tool detection circuit (80, 380 or 480), an estimate of the color space encountered during a "typical" video assisted procedure is obtained and quantified. As shown by FIG. 5, an approach for estimating the color space is to sample a wide range of video tape or camera output taken during different "simulated" or real video assisted procedures. For example, a laparoscopic procedure may be simulated by using the laparoscope 40 and tool 20 in an animal specimen.

The system for collecting training data includes a VCR 502 and/or color imager 504, a color separator 506, and a data acquisition and image analysis system 508. The analysis system 508 is capable of operating at video rates and may be implemented in a computer, such as a personal computer. The raw video data are converted to a digital representation by color separator 506. The data from each captured frame are then mapped to a color space histogram and are stored in a file in the computer 508. It is expected that the color data will be procedure specific; a different histogram may be observed for each type of procedure. Each file is then combined into a composite color map of video assisted procedures. The composite color map represents the estimate of the color space probability density function for video assisted procedures.

Having constructed the estimate of the color map probability density function, an analysis is performed to search the color space for those colors which have potential for use as the marker color for tool 20. Additional information may also be extracted for such pertinent design parameters as color space quantization and variability of the different video sources. The analysis may be followed by simulation of the various detection algorithms described above and calculation of expected system performance.

Preferably, the color chosen differs from any tissue in the peritoneal cavity sufficiently that there is little difficulty in detecting the presence of the selected color in the viewed image. For example, the inventors have determined that markers having a predetermined color of pure green and blue (either by emission or reflection) possess this characteristic. (Details of the inventor's analysis of green and blue markers are provided below with reference to FIGS. 7-11). It may be desirable to program the control mechanism 89 (FIG. 1) to recognize more than one tool color. In this case, a calibration procedure could include exposing the laparoscope 40 to the tool 20 within a calibration chamber (not shown) that has a known fixed color and reflectance, to identify the color range of the tool before beginning the video assisted procedure.

Experiments were performed to determine the expected performance of a color detection scheme for use as an electrosurgical interlock in power generators. The results showed that using color as an identification method provides a highly reliable, inexpensive means to achieving this objective.

Attention was centered on the issue of detector sensitivity given the wide variety of video assisted surgery camera and lighting systems and their ability to reproduce a consistent electronic representation of the probe color. Initially, green had been selected as the marker color. Experiments showed that, although green performed well as a detectable color, variance existed between the two camera systems used. This suggested that a broader range of camera/lighting systems should be analyzed.

The experiments showed that the preferred color for the marker 22 is blue. The blue used during the experiments was selected from a series of Panatone color samples and is known as Process Blue U. The decision to select blue over green for video assisted surgical procedures was based upon the results of a variance analysis of the data taken from a combination of six cameras and three lighting systems.

Table 1 lists the chromaticity components and values detected from a blue sample, using three light sources and six cameras. In Table 1, the values r, b and g are defined by:

$$r = R/(R+B+G)$$

$$b = B/(R+B+G)$$

$$g = G/(R+B+G)$$

where R, B and G are the red, blue and green components provided by color separator 60, shown in FIG. 1. Thus r, b and g provide information about hue and saturation, but not brightness.

TABLE 1

| light | camera | r | b | g | variance source |
|---|---|---|---|---|---|
| 1 | 1 | 11 | 49 | 40 | 5 |
| 1 | 2 | 0 | 71 | 29 | 5 |
| 1 | 3 | 4 | 56 | 40 | 5 |
| 1 | 4 | 0 | 62 | 38 | 3 |
| 1 | 5 | 1 | 60 | 40 | 3 |

TABLE 1-continued

| light | camera | r | b | g | variance source |
|---|---|---|---|---|---|
| 1 | 6 | 1 | 64 | 35 | 3 |
| 2 | 1 | 6 | 55 | 39 | 7 |
| 2 | 2 | 0 | 68 | 31 | 2 |
| 2 | 3 | 2 | 57 | 41 | 3 |
| 2 | 4 | 0 | 63 | 36 | 3 |
| 2 | 5 | 0 | 59 | 41 | 3 |
| 2 | 6 | 0 | 62 | 38 | 2 |
| 3 | 1 | 3 | 56 | 40 | 3 |
| 3 | 2 | 0 | 68 | 31 | 2 |
| 3 | 3 | 2 | 57 | 41 | 3 |
| 3 | 4 | 0 | 63 | 36 | 3 |
| 3 | 5 | 0 | 58 | 42 | 3 |
| 3 | 6 | 3 | 56 | 40 | 3 |

Figure 7:
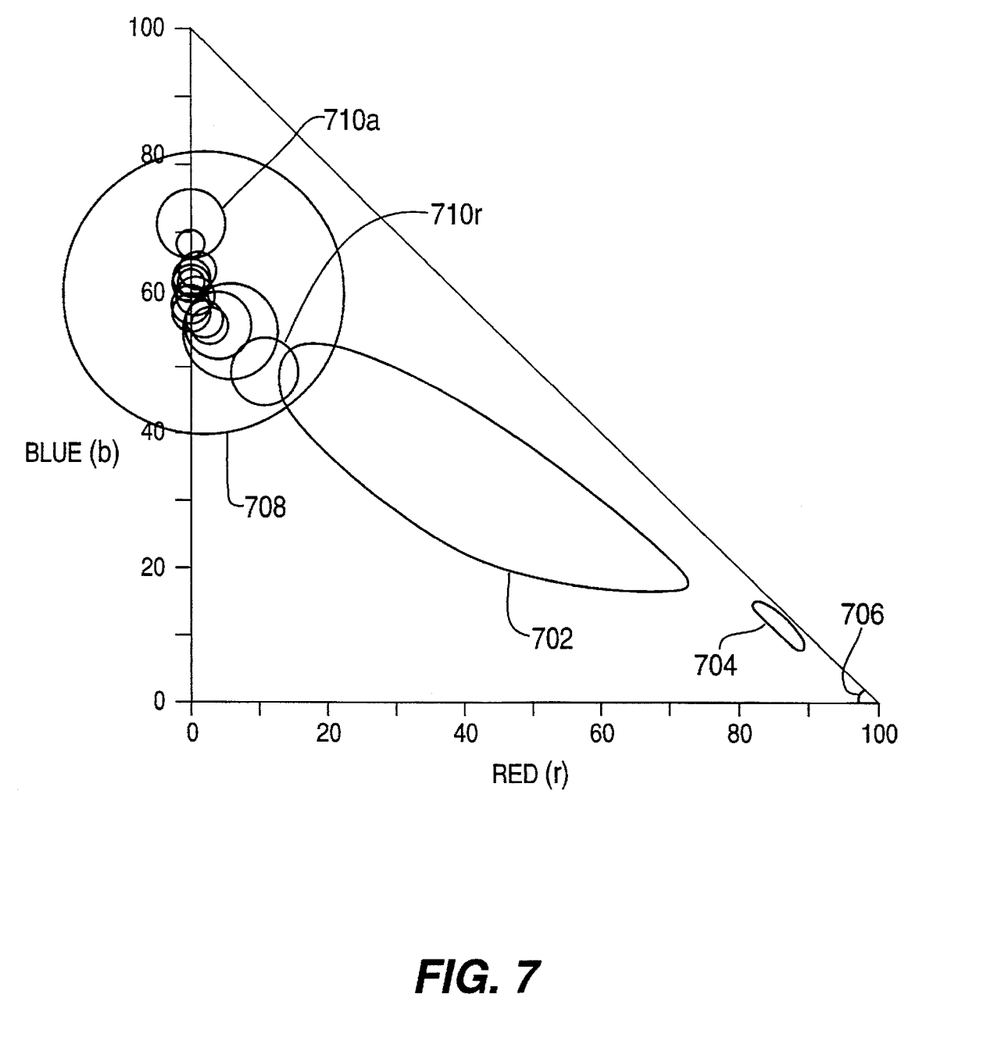
FIG. 7 is a chromaticity diagram showing the background color space for imager assisted surgical procedures, and the detected colors in a blue marker as shown in FIG. 1.

FIG. 7 is a chromaticity diagram showing the relative values of the background color space for video assisted surgical procedures and the light detected from the blue marker during testing. The coordinate axes shown in FIG. 7 are r and b as determined for Table 1. FIG. 7 includes a respective circle 710a–710r for each row of Table 1. Only the circles 710a and 710r with the highest and lowest blue component b, respectively, are labeled with reference numerals. The circles 710a–710r have their respective centers located at X and Y coordinates equal to the r and b values for each row of Table 1. The radius of each circle 710a–710r is equal to the variance in the corresponding row in Table 1. The circle 708 indicates the expected color space for blue markers based on the test data. This data may be used to set the minimum and maximum threshold values used by the color detector, such as the one shown in FIG. 6. With reference to the detector of FIG. 6, this may be done by defining the smallest square (not shown) which includes all of the circles 710a through 710r. The Blue coordinates of the horizontal lines of the square define the upper and lower thresholds for the B/(R+B+G) signal and the red coordinates of the vertical lines define the upper and lower thresholds for the R/(R+B+G) signal.

FIG. 7 also shows the color space for the background in video assisted surgical procedures. The color space for VAP is indicated by regions 702, 704 and 706. Regions 702, 704 and 706 indicate all of the colors which appeared in more than 1000 pixels in a sample including 120 images (including a total of 36,864,000 pixels). Regions 702, 704 and 706 are substantially disjoint from the blue color space circle 708.

The results of the analysis showed that green would prove to be less reliable as a detectable color due to the high coincidence of background color that fall within the calculated search range. That is, a detector that searches for a green marker is more likely to cause false alarms.

The same analysis for the color blue showed a high degree of reliability as a detectable color. Working within the parameters of the detection system, it should be possible to reduce the false alarm rate to less than one part in one hundred thousand (i.e. approximately once every 55 minutes) while employing a Process Blue U probe tip whose length is between one half inch and one inch long (1.25 to 2.5 centimeters). It was also demonstrated that blue provides slightly better performance with respect to detection than green. That is, the probability of correctly identifying the marker 22 as being present is slightly higher for a blue marker than for a green one.

Field of view measurements were made to determine necessary marker lengths. This experiment was performed at four different magnifications wherein a laparoscope was held at half inch, one inch, two inch, and three inches above the object to simulate the range a surgeon might use during a laparoscopic procedure. The percentage field of view was calculated for a variety probe sizes. The percent field of view of the marker 22 is an important parameter with respect to detection of the probe because it represents the magnitude of the signal relative to the background colors (i.e. noise). Probability of detection is directly proportional to the amount of signal available to the detection circuit and increases as the percent field of view increases for the marker 22. The marker lengths used for the experiments were one quarter inch, one half inch, and one inches.

Images of ten color chips were gathered using combinations, each combination comprising one of three light sources and one of six cameras. Color histograms of the samples showing mean and variance for each camera-light source combination were plotted. These data define the ability of each of the six cameras to reproduce known colors when illuminated with three different types of light sources.

From this large collection of data, the images representing blue and green were analyzed for camera variance for each of the light sources. It was found that green has a much wider variance than blue. This result led to the conclusion that the color blue is a more desirable choice for the color of marker 22.

Color histograms of one hundred and twenty images from two light sources and six cameras were analyzed to provide a better estimate of the background in which the probes are to be detected.

The objective was to determine the robustness of the color detection algorithm for use as a laparoscopic interlock. The results of the following analysis shall show conclusively that given a blue marker color, the detection algorithm is effective.

The first step toward demonstrating the algorithm's reliability was to determine the signal to noise ratio for the candidate colors, green and blue. This was accomplished using the following procedure:

1. Determine mean and standard deviation for candidate color given all camera/light source combinations.
2. Search the background colorspace for the occurrence of the marker color in 'typical' laparoscopic scenes within a search range defined by the mean marker color and its standard deviation.
3. Search the colorchip data to find the relative number of occurrences within the search range defined by the mean marker color and its standard deviation
4. Repeat steps one through three for integer numbers of standard deviations.

Figure 8:
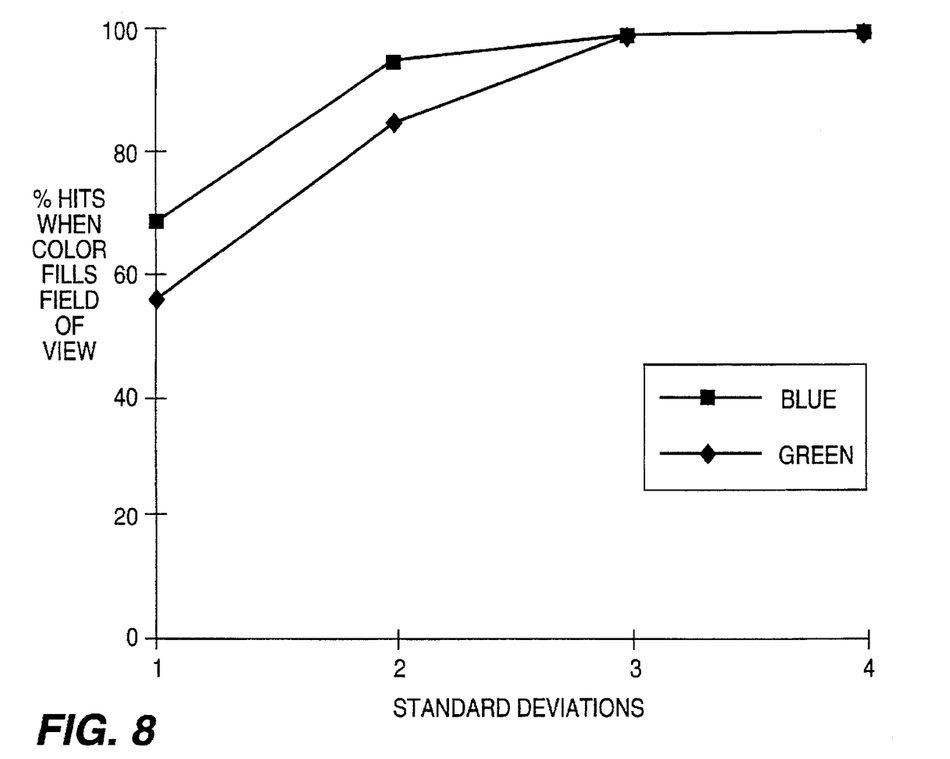
FIG. 8 is a graph showing percentage of correct detections when a marker fills the field of view of the imager of FIG. 1.

The results of this procedure are shown in FIG. 8. FIG. 8 is a graph showing the percentage of occurrences wherein the marker 22 is known to fill the full field of view of the imager system, and the system identifies the marker 22 as being present. As shown in FIG. 8, the data for green and blue closely follow one another; in each case, 99% of all pixels are detected when the search range is expanded to encompass three standard deviations. In practice, this means there is a 99% probability that either marker color is detected if present in the scene.

Figure 9:
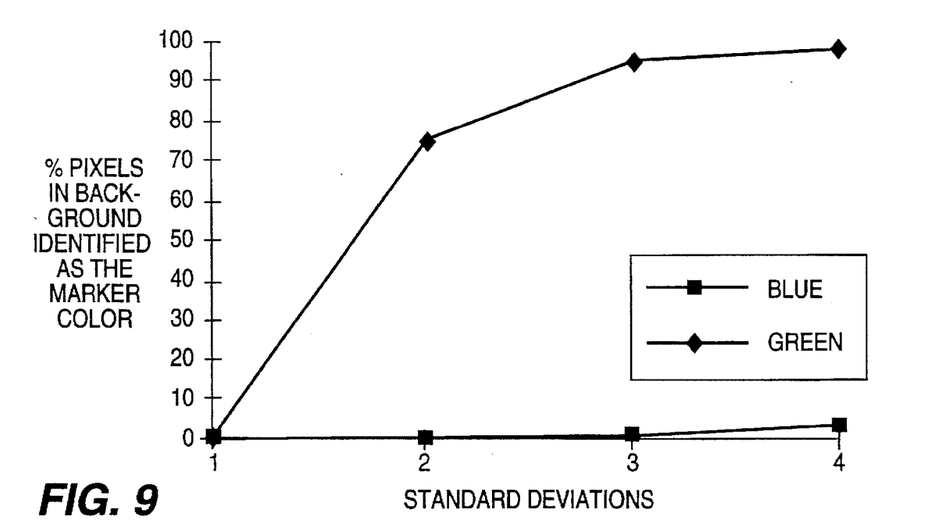
FIG. 9 is a graph showing the percentage of pixels falsely detected when the marked object is outside the field of view of the imager of FIG. 1.

FIG. 9 is a graph showing the 'average' probability of occurrence that the selected color appears in a 'typical' laparoscopic scene when the marker is not within the field of view. This is an indicator of the likelihood of a false alarm if a particular color is used for the marker 22. As is apparent from FIG. 9, the color blue excels with respect to this measurement and provides a high degree of confidence that the interlock system will work with high reliability. The experiment showed wide variations between camera and light source combinations for the color green. When searching for green, the probability of detection increases rapidly as the range of wavelengths expands. As a result, at a distance of two standard deviations from the mean of the search range, 60% of all image pixels would be identified as being within the range of the marker color). Quite a different situation is found when the color blue is used for marker 22. When a search range of three standard deviations from the mean wavelength is used to search the background (while the marker 22 is not within the field of view), only 0.55% of all background pixel exhibit the color blue.

Therefore, although both blue and green provide a high probability of detection when the marker 22 is within the field of view, green has a high probability of producing a false alarm when the marker is not present. Blue, on the other hand, provides excellent false alarm avoidance.

Further analysis of the background noise data was performed to provide estimates of the probability of detection when the marker 22 is known to be within the field of view and when it is known that the marker 22 is not within the field of view. The analysis consisted of creating a distribution of the detected hits within the search range for each of the background images. Two separate distributions were developed for this purpose after finding that one of the parameters of the search, (i.e. minimum luminance threshold) affected the results.

Figure 10A:
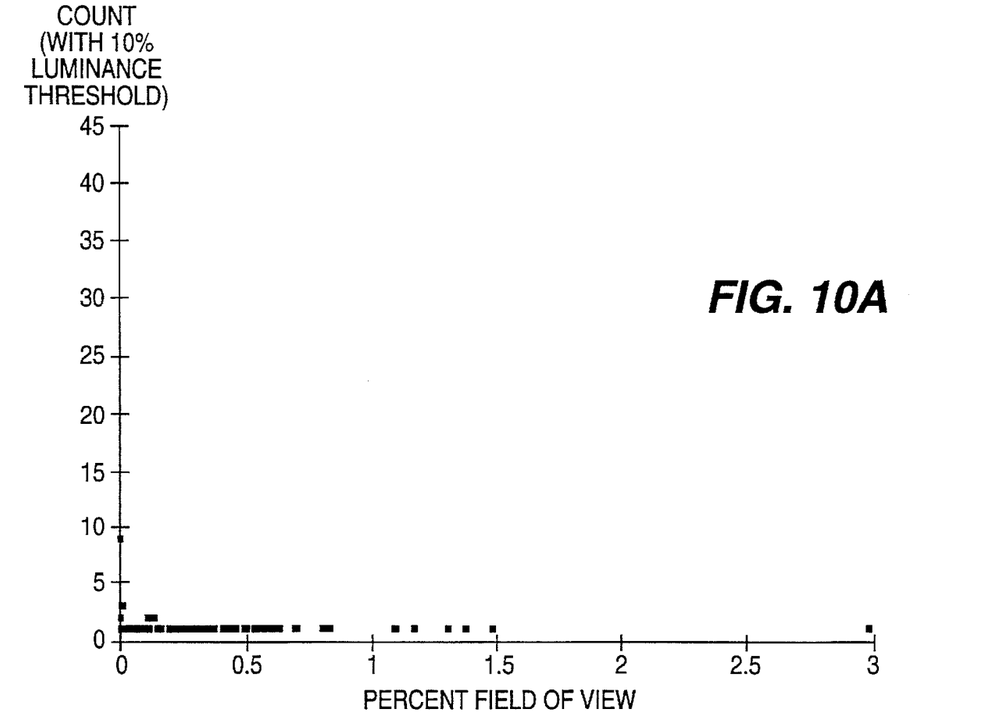
FIGS. 10A and 10B are diagrams showing the number of background pixels identified as being blue when the marked object is outside the field of view of the video system shown in FIG. 1.

FIG. 10A is a graph showing the distribution of background pixels identified as blue while the marker 22 was not within the field of view as a function of the size of the region or object. A luminance threshold of 10% of the full signal range was used for the data of FIG. 10A. FIG. 10A shows that a region as large as 3.0% of the field of view was identified as blue. Thus a minimum area of 3.0% of the field of view having the color blue would be necessary to avoid false detection of the marker 22 with a 10% luminance threshold.

Figure 10B:
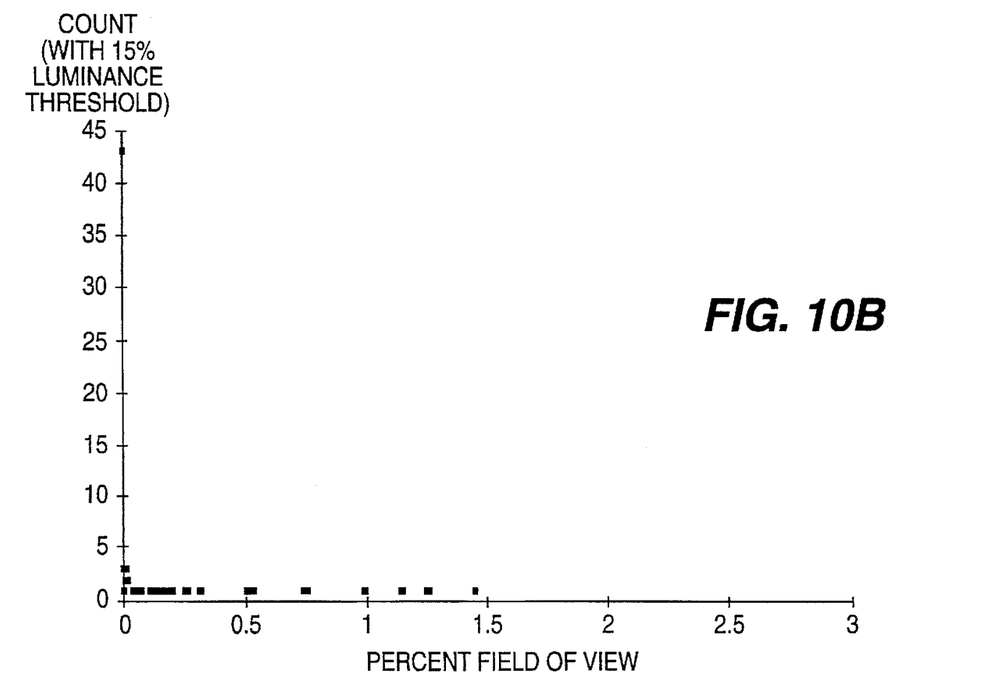

FIG. 10B is a graph showing the distribution of background pixels identified as blue while the marker 22 was not within the field of view when a luminance threshold of 15% of the full signal range was used. When the 15% threshold was used, no background regions greater than 1.5% of the field of view were identified. Thus, better noise statistics were produced when the luminance threshold was raised to 15% of the full range signal. By requiring that a blue region cover at least 1.5% of the field of view and using a luminance threshold of 15%, false detections may be avoided.

The mean and standard deviation for each of the distributions in FIGS. 10A and 10B were calculated These values are used to estimate the probability of detection and false alarm. The mean of the fifteen percent luminance data shown in FIG. 10B is 0.11% of the field of view and the standard deviation was calculated to be 0.28% field of view. The mean of the ten percent luminance distribution shown in FIG. 10A was found to be 0.23% field of view and the standard deviation was calculated to be 0.41% field of view. These results may be used to quantify the 'expected' performance of a laparoscopic detection system and the requirements of the colored marker for the probe tip.

Figure 11:
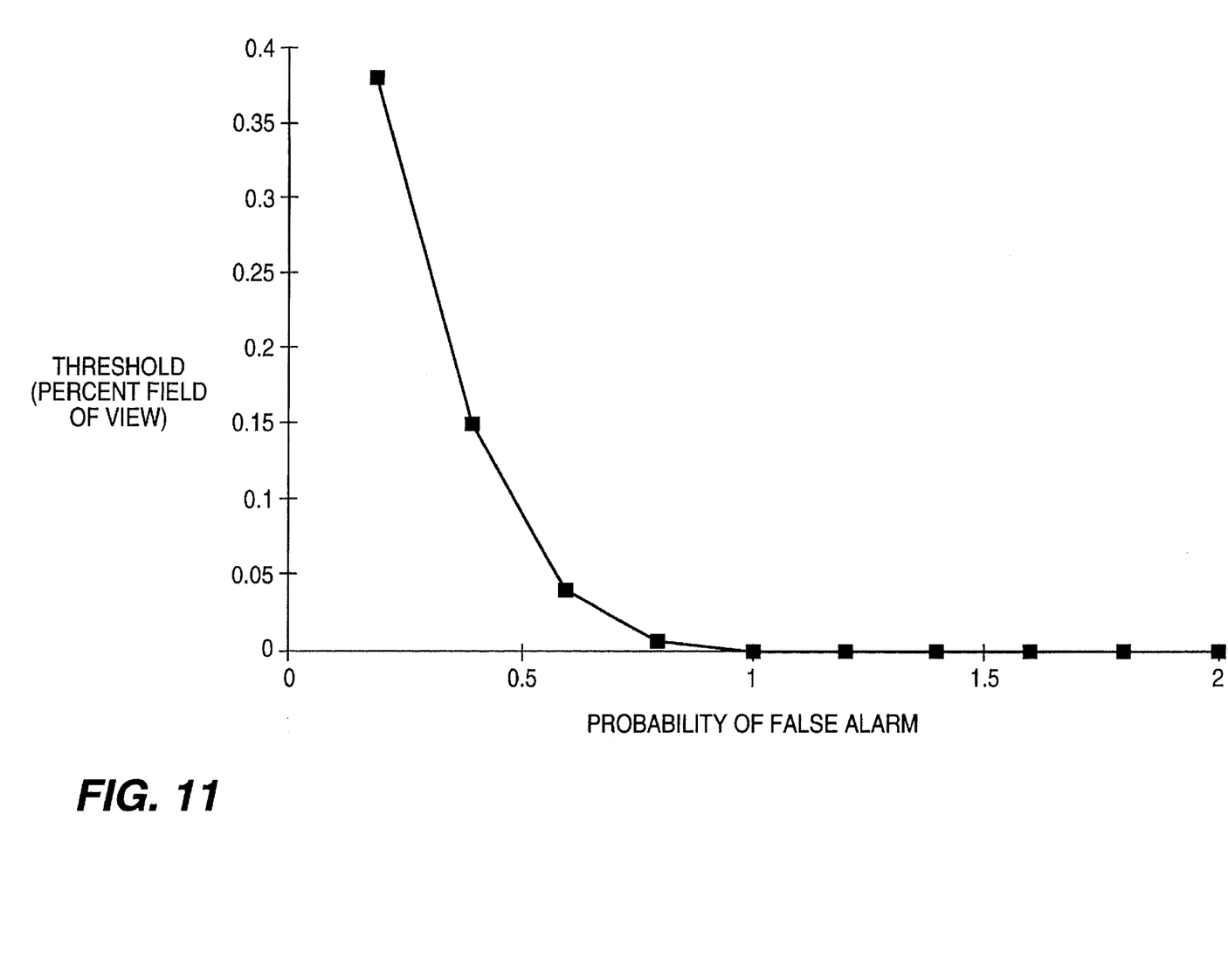
FIG. 11 is a graph showing the probability of generating a false alarm (indicating the presence of the color blue) when the marked object is outside the field of view of the video system shown in FIG. 1.

The probability of false alarm, that is, the case in which the marker is not within the field of view but is detected, may be directly calculated from the noise statistics, based on one of the selected luminance thresholds. Assuming that the noise data represent a subsample from a Gaussian distribution, and that the mean and standard deviation of these data are good estimates of that distribution, the probability of false alarm may be calculated for a range of threshold values. FIG. 11 is a graph showing the estimated probability of false alarm as a function of a minimum field of view threshold.

The probability of detection is a function of the marker size. As shown in FIG. 8, the probability that the marker color is detected if the marker fills the field of view) given a wavelength range of three standard deviations about the mean wavelength searched for) is 99.3%. Therefore, the fraction of the field of view identified as the marker 22 is directly proportional to the marker size and the threshold used for detection. The inventors have determined that a marker length of 1.5 inches and a threshold value of 1.5–2.0% of the field of view are acceptable.

Although the apparatus has been described with reference to a marker 22 having a single predetermined color, the probability of avoiding a false detection may be enhanced by using a marker 22 comprising two distinct portions, each having a unique color. For example, the marker 22 may include a band of blue and a band of green. The system only identifies the marker 22 as being present if both colors are detected.

A simple system using two colors may include two color detectors 70, similar to the color detectors shown in FIG. 6. Each detector 70 would have a unique set of values LOWREF1, HIGHREF1, LOWREF2, and HIGHREF2 to define a color range for each respective predetermined color. The output signal from each of the two color detectors 70 would be transmitted to an AND gate (not shown). The output signal of the AND gate would only be logic high if both colors are detected.

A more complex system using two colors may also include spatial filtering. For example, in addition to requiting the presence of both colors, the system could require that both colors be found within a predetermined distance of one another before indicating that the marker 22 is present.

Another alternate processing method (not shown) involves converting the R, G and B data to hue, saturation, Luminance (HSL) data. A mask is generated from the H plane which isolates the hue(s) of interest. The mask is applied to the L plane, blanking out all regions which do not correspond to the hue(s) of interest. A threshold operator is applied to the L plane, so that only pixels which have the correct hue and a brightness above the threshold remain. An erosion operator is then applied to the L plane, essentially eliminating one pixel from each set of contiguous pixels having the correct hue and brightness. This eliminates all single pixels from the solution set. Only objects larger than one pixel remain. Similarly, if the object is large, then objects smaller than a threshold number of pixels (N) in size may be deleted from the solution set by repeating the erosion step N times. The remaining pixels are identified as the marker 22.

Although the apparatus has been described with reference to an interlock control system for an electrosurgical tool, the invention may be applied in a variety of control systems. For example, the invention may be used for controlling a robotic system (not shown) that applies a tool (e.g., a laser, a cutter, a welding gun, or a paint gun, etc.) to transform a workpiece. A robotic system in accordance with the invention may include a marker having a predetermined color applied to an instrument (a laser, a cutter, a welding gun, or paint gun) to form a marked device. An imager, such as a video camera, that is used to delimit the work area (and which may also be used to guide the robot to the location of the workpiece), generates imager signals representing a color image of the field of view of the imager. The color separator 60, color detection mechanism 70 and interlock control system 80 work in the same manner described above with reference to FIGS. 2–4. Thus, the robot can only actuate the device while the device is within the field of view of the imager.

More generally, the invention may be practiced in any system or situation that includes (1) a color detection mechanism for supplying color image data from which the position of an object within the field of view of the color detection mechanism may be detected; and (2) an instrument that is either operated by a human operator or automatically controlled, wherein the human or automatic control system uses position data from the color detection mechanism to determine the position of the device.

Although the apparatus is most cost effective in systems that already include a video detection system (such as in a laparoscopic system), the hardware used to practice the invention may also be added for the specific purpose of providing a safety cutoff mechanism for an instrument. For example, a video detection mechanism may be installed in a piece of headgear worn by a skilled worker machining an expensive workpiece (e.g., cutting diamonds). A control system in accordance with the invention would automatically disable the tool used to machine the workpiece if the worker's head turns so that the workpiece is outside of the field of view of the detection mechanism.

Although the invention has been described with reference to exemplary embodiments, it is not limited thereto. Rather, the appended claims should be construed to include other variants and embodiments of the invention which may be made by those skilled in the art without departing from the true spirit and scope of the present invention.

We claim:

1. Apparatus for controlling a device, said apparatus comprising:

a marker having a predetermined color and being applied to the device to form a marked device;

an imager which generates imager signals representing a color image of a region proximate to the imager;

a detector which processes the imager signals to detect a range of colors, which includes the predetermined color, in the image represented by the signals and for providing an output signal representing instances of imager signals in the detected color range;

detection means for processing the output signal of the color detector to provide an indication of whether the output signal of the color detector conforms to the marked device, thereby to indicate whether the marked device is included in the color image represented by the imager signals; and control means responsive to the detection means for disabling the marked device whenever the detection means indicates that the marked device is not in the color image, and for allowing the marked device to be enabled whenever the detection means indicates that the marked device is in the color image.

2. The apparatus of claim 1, wherein the detection means comprises:

means for counting a number of pixels within the detected color range in a single frame of said imager signals, based on said output signal, and means for indicating that the detected instances conform to the marked device if the number of pixels exceeds a predetermined threshold value.

3. The apparatus of claim 1, wherein the detection means comprises:

means for estimating a contour of the marked device, means for determining a number of pixels that are within the detected color range and within said contour, in a single frame of said imager signals, based on said output signal, and means for indicating that the detected instances conform to the marked device if the number of instances exceeds a predetermined threshold value.

4. The apparatus of claim 3, wherein said determining means includes spatial filter means for extracting spatial features from the output signal to determine whether said detected instances conform to said marked device.

5. The apparatus of claim 1, wherein the device is a surgical tool.

6. The apparatus of claim 1, further comprising a laparoscope having a field of view and coupled to the imager for providing the color image to the imager, wherein:

the device is an electrosurgical tool, and the control means includes means for disabling the electrosurgical tool if the electrosurgical tool is outside the field of view of the laparoscope.

7. The apparatus of claim 6, wherein the predetermined color is blue.

8. Apparatus for controlling a device that is applied to transform a specific object, said apparatus comprising:

a marker having a predetermined color and being applied to the device to form a marked device;

an imager which generates imager signals representing a color image of a region proximate to the imager;

means for selecting a subset of said imager signals to form a reduced area image of the region;

a color detector which processes the subset of the imager signals to detect a range of colors, which includes the predetermined color, in the reduced area image represented by the subset of the imager signals and for providing an output signal representing instances of imager signals in the detected color range;

detection means for processing the output signal of the color detector to provide an indication of whether the output signal of the color detector conforms to the marked device, thereby to indicate whether the marked device is included in the reduced area image represented by the imager signals; and control means responsive to the detection means for disabling the marked device whenever the detection means indicates that the marked device is not in the reduced area image, and for allowing the marked device to be enabled whenever the detection means indicates that the marked device is in the reduced area image.

9. Apparatus for controlling a tool that is used to cut tissue during surgery, said apparatus comprising:

a marker having a predetermined color and being applied to the tool to form a marked tool;

a laparoscope having a field of view which includes a region in which the tissue to be cut during surgery is located and receives light therefrom;

an imager coupled to receive light from the laparoscope and generate imager signals representing a color image of the field of view of the laparoscope;

a color detector which processes the imager signals to detect a range of colors, which includes the predetermined color, in the image represented by the imager signals and for providing an output signal representing instances of imager signals in the detected color range;

detection means for processing the output signal of the color detector to provide an indication of whether the output signal of the color detector conforms to the marked tool, thereby to indicate whether the marked tool is in the field of view of the laparoscope; and control means responsive to the detection means for disabling the marked tool whenever the detection means indicates that the marked tool is outside the field of view of the laparoscope, and for allowing the marked tool to be enabled whenever the detection means indicates that the marked tool is within the field of view of the laparoscope.

10. The apparatus of claim 9, wherein the predetermined color is blue.

11. A method for controlling a device that is applied to transform a specific object, said method comprising the steps of:

(a) applying a marker having a predetermined color to the device to form a marked device;

(b) generating imager signals which represent a color image of a region proximate to the imager;

(c) detecting a range of colors in the color image represented by the imager signals, said range of colors including the predetermined color;

(d) forming an output signal representing instances of imager signals in the detected color range;

(e) processing the output signal to provide an indication of whether the output signal of the color detector conforms to the marked device, thereby identifying whether the marked device is included in the color image represented by the imager signals;

(f) disabling the marked device whenever the indication identifies the marked device as not being included in the color image represented by the imager signals; and (g) allowing the marked device to be enabled whenever the indication identifies the marked device as being included in the color image represented by the imager signals.

12. A method according to claim 11, wherein step (c) includes the steps of:

analyzing said output signal to determine a number of pixels within the detected color range in a single frame of said imager signals, and indicating that the detected instances conform to the marked device if the number of pixels exceeds a predetermined threshold value.

13. The method of claim 11, wherein step (c) includes the steps of:

estimating a contour of the marked device, analyzing said output signal to determine a number of pixels that are within the detected color range and within said contour, in a single frame of said imager signals, and indicating that the detected instances conform to the marked device if the number of instances exceeds a predetermined threshold value.

14. The method of claim 11, wherein the imager is coupled to an instrument which has a field of view and provides the color image to the imager, the device is a tool, and step (f) includes:

disabling the tool if the tool is outside the field of view of the instrument.

15. The method of claim 14, further comprising executing the following steps before step (b):

(1) sampling a plurality of training imager signals during at least one surgical procedure;

(2) extracting color histogram data from the sampled training imager signals; and (3) identifying the range of colors based on the color histogram data.

16. The method of claim 14, further comprising executing the following steps before step (b):

(1) sampling training imager signals during first and second surgical procedures;

(2) extracting a first set of color histogram data from the training imager signals sampled during the first surgical procedure, and a second set of color histogram data from the training imager signals sampled during the second surgical procedure;

(3) combining the first and second sets of color histogram data to form a composite color space probability density function; and (4) identifying the range of colors based on the composite color space probability density function.

17. The method of claim 11, wherein the predetermined color is blue.

* * * * *